US00PP11030P

United States Patent [19]

Brown

[11] Patent Number: Plant 11,030

[45] Date of Patent: Aug. 10, 1999

[54] AGLAONEMA PLANT NAMED 'BRILLIANT'

[75] Inventor: B. Frank Brown, Valkaria, Fla.

[73] Assignee: Sunshine Foliage World, Zolfo Springs, Fla.

[21] Appl. No.: 09/004,128

[22] Filed: Jan. 7, 1998

[51] Int. Cl.[6] ..... A01H 5/00

[52] U.S. Cl. ..... Plt./376

[58] Field of Search ..... Plt./376

*Primary Examiner*—Howard J. Locker
*Assistant Examiner*—Melissa L. Kimball
*Attorney, Agent, or Firm*—C. A. Whealy

[57] ABSTRACT

A new and distinct cultivar of Aglaonema named 'Brilliant' particularly characterized by its mostly upright and somewhat outwardly arching plant habit; propensity to readily produce divisions; upper leaf surfaces that are glossy silver green with white, yellowish green, light green and dark green streaks and spots; light green to white midveins; oblong and broad leaf shape; white petioles; low-temperature tolerance; and resistance to diseases common to Aglaonema.

1 Drawing Sheet

The present invention relates to a new and distinct cultivar of Aglaonema plant, botanically known as Aglaonema hybrid, and hereinafter referred to by the cultivar name Brilliant.

The new Aglaonema is a product of a planned breeding program conducted by the inventor in Valkaria, Fla. The objective of the breeding program was to develop new Aglaonemas with unique and interesting leaf patterns and that produce numerous divisions. The new Aglaonema originated from a cross made by the inventor in 1991 of the Aglaonema hybrid cultivar Manila Pride (not patented) as the female, or seed, parent with the Aglaonema hybrid cultivar Mona Lisa (not patented) as the male, or pollen, parent. The cultivar Brilliant was discovered and selected by the inventor as a seedling within the progeny of the stated cross in a controlled environment in Valkaria, Fla.

Compared to plants of the female parent cultivar, Manila Pride, plants of the new Aglaonema are much shorter and produce significantly more divisions. In addition, plants of the cultivar Manila Pride have pink petioles whereas plants of the new Aglaonema have white petioles.

Compared to plants of the male parent cultivar, Mona Lisa, plants of the new Aglaonema produce significantly more divisions and are much more cold-tolerant. In addition, plants of the cultivar Mona Lisa have green petioles whereas plants of the new Aglaonema have white petioles.

Asexual propagation of the new cultivar by divisions at Zolfo Springs, Fla., since 1992, has shown that the unique features of this new Aglaonema plant are stable and reproduced true to type in successive generations.

The new Aglaonema has not been observed under all possible environmental conditions. The phenotype may vary somewhat with variations in environment such as temperature, light intensity, fertilizer rate, and/or irrigation amount and frequency without, however, any variance in genotype.

The following traits have been repeatedly observed and are determined to be the unique characteristics of 'Brilliant'. These characteristics in combination distinguish 'Brilliant' as a new and distinct cultivar:

1. Plants of the new Aglaonema are mostly upright and somewhat outwardly arching in plant habit.
2. Plants of the new Aglaonema readily produce divisions.
3. The upper surfaces of mature leaves of plants of the new Aglaonema are glossy silver green with white, yellowish green, light green and dark green streaks and spots. Midveins are light green to white.
4. The leaves of the new Aglaonema are oblong and broad.

5. Mature leaves of plants of the new Aglaonema have white petioles.
6. Plants of the new Aglaonema are tolerant of low termperatures, that is, ambient temperatures of about 7° C. do not cause foliar damage.
7. Plants of the new Aglaonema are resistant to diseases common to Aglaonema.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical plant of 'Brilliant' in a 25.5-cm container.

The photograph at the bottom of the sheet comprises a close-up view of the upper surface of a mature leaf. Leaf colors in the photographs may appear different from the actual colors due to light reflectance.

DETAILED BOTANICAL DESCRIPTION

The following observations, measurements and comparisons describe plants grown in Zolfo Springs, Fla., under a polypropylene-covered shadehouse and conditions which closely approximate those used in horticultural practice. Plants were grown under day temperatures ranging from 21 to 38° C. and night temperatures ranging from 7 to 21° C. The polypropylene shade provided a 84 percent decrease in ambient light level. In the following description, color references are made to The Royal Horticultural Society Colour Chart except where general terms of ordinary dictionary significance are used.

Botanical classification: Aglaonema hybrid cultivar Brilliant.

Parentage:

*Female, or seed, parent.*—Aglaonema hybrid cultivar Manila Pride, not patented.

*Male, or pollen, parent.*—Aglaonema hybrid cultivar Mona Lisa, not patented.

Propagation:

*Type.*—By division and by cuttings.

*Time to initiate roots.*—About 26 and 37 days at 30 and 21° C., respectively.

*Time to develop roots.*—About 38 and 44 days at 30 and 21° C., respectively.

*Rooting habit.*—Numerous thick, fleshy, white roots.

Plant description:

*Plant shape.*—Mostly upright and somewhat outwardly arching.

*Growth habit.*—Erect when young, becoming somewhat outwardly arching. Appropriate for 25.5-cm containers. Readily produces divisions.

*Plant size.*—Height, soil surface to top of leaf canopy: About 64 cm. Width: About 68 cm.

*Plant vigor.*—Moderate.

*Stem description.*—Diameter at soil surface: About 2.25 cm. Internode length: About 1.75 cm. Color, mature: Yellowish green.

*Foliage description.*—Shape: Oblong, broad. Length, fully expanded: About 32 cm. Width, fully expanded: About 13 cm. Margin: Entire. Apex: Acuminate. Base: Cuneate. Aspect: Mostly flat. Texture: Leathery, smooth, glabrous, glossy on both surfaces. Color: Young, upper surface: Background: Silver green, close to 191B/194B. Green spots/streaks: 144A. Yellowish green spots/streaks: About 150B/150C. White spots/streaks: 155A and 150D. Young, lower surface: Background: Green, 146B/146C. White spots/streaks: 155A. Mature, upper surface: Background: Silver green, close to 191A. Dark green spots/streaks: 147A to darker than 147A. Light green and yellowish green spots/streaks: 144A, 154A, and 150A/150B/150C. White spots/streaks: 155A and 150D. Mature, lower surface: Background: Green, close to 146A. White spots/streaks: 155A and 150D. Petiole length, primary shoot: About 23 cm. Petiole diameter at apex: About 7 mm. Petiole diameter at base: About 1.25 cm. Petiole wing: Apparent on lower 67% of mature leaf petiole, about 15 cm in length and about 7.5 mm in width. Petiole color: Young: Light green, 145C/145D. Mature: Mostly white, 155A. Venation, midvein: Immature, upper surface: Light green, 145C. Immature, lower surface: Light green, 145D. Mature, upper surface: Light green, 145C/145D, to white, 155A. Mature, lower surface: White, 155A.

*Inflorescence.*—Typical of Aglaonema, no commercial significance.

Disease tolerance: Plants of the new Aglaonema are resistant to diseases common to Aglaonema.

Low temperature tolerance: Plants of the new Aglaonema are tolerant of low temperatures, that is, ambient temperatures of about 7° C. do not cause foliar damage.

It is claimed:

1. A new and distinct cultivar of Aglaonema plant named 'Brilliant', as illustrated and described.

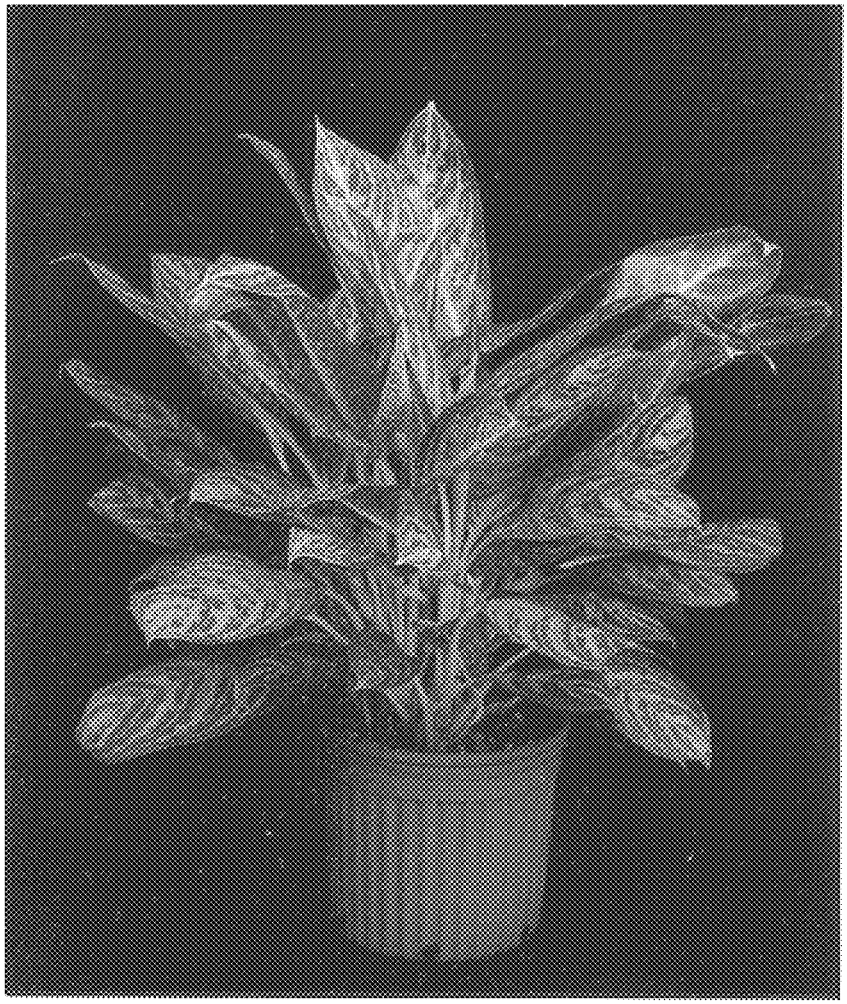
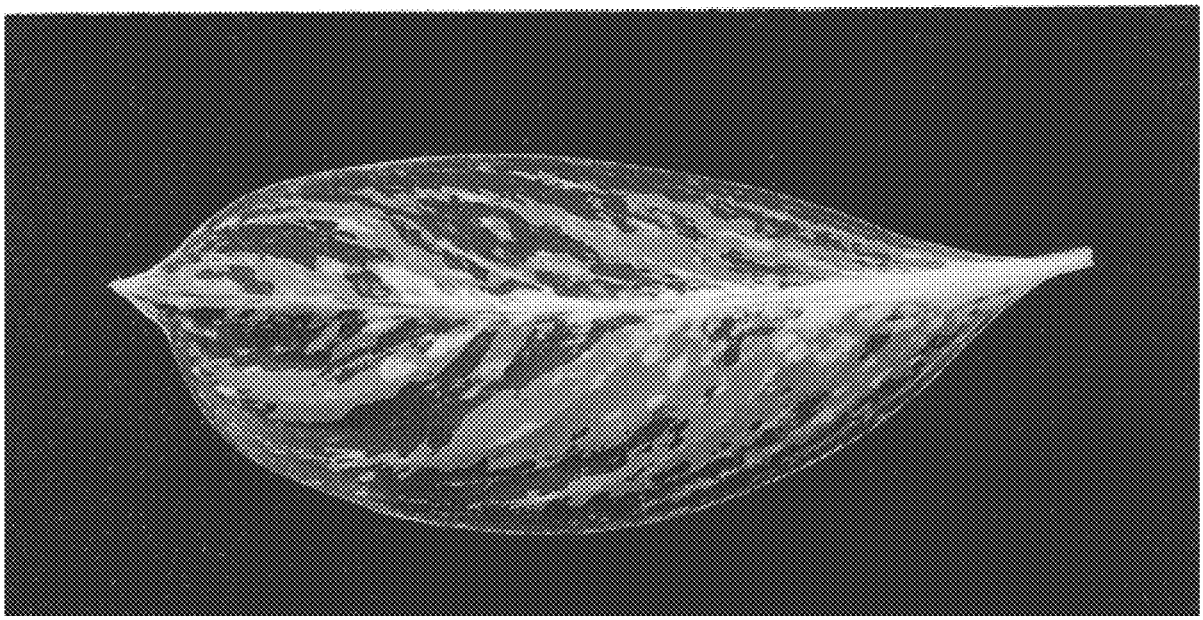

* * * * *